United States Patent [19]
Colaco et al.

[11] Patent Number: 6,034,080
[45] Date of Patent: *Mar. 7, 2000

[54] USE OF MAILLARD REACTION INHIBITORS FOR THE TREATMENT OF AMYLOIDOSIS-BASED DISEASE

[75] Inventors: Camilo Colaco, Trumpington; Bruce Joseph Roser, Cambridge, both of United Kingdom

[73] Assignee: Quadrant Holdings Cambridge Limited, United Kingdom

[ * ] Notice: This patent is subject to a terminal disclaimer.

[21] Appl. No.: 09/205,329

[22] Filed: Dec. 4, 1998

Related U.S. Application Data

[63] Continuation of application No. 08/727,597, filed as application No. PCT/GB95/00843, Apr. 13, 1994, Pat. No. 5,891,873.

[30] Foreign Application Priority Data

Apr. 13, 1994 [GB] United Kingdom ................... 9407305

[51] Int. Cl.[7] ........................ A61K 31/535; A61K 31/70; A61K 31/47; A61K 31/155
[52] U.S. Cl. ........................ 514/229.8; 514/31; 514/311; 514/634
[58] Field of Search ................................ 514/229.8, 311, 514/31, 634

[56] References Cited

U.S. PATENT DOCUMENTS

| | | | |
|---|---|---|---|
| 5,112,596 | 5/1992 | Malfroy-Camine | 424/9.1 |
| 5,202,333 | 4/1993 | Berger et al. | 514/296 |
| 5,403,861 | 4/1995 | Goldin et al. | 514/634 |
| 5,422,360 | 6/1995 | Miyajima et al. | 514/391 |
| 5,453,514 | 9/1995 | Niigata et al. | 548/362.5 |
| 5,891,873 | 4/1999 | Colaco et al. | 514/229.8 |

FOREIGN PATENT DOCUMENTS

| | | |
|---|---|---|
| 0 474 874 | 3/1992 | European Pat. Off. . |
| WO 95/20979 | 8/1995 | WIPO . |

OTHER PUBLICATIONS

Pocchiari, M. et al., "Amphotericin B: A Novel Class of Antiscrapie Drugs," *J Infect Dis* (1989) 160(5):795–802.

Brown, P., "A Therapeutic Panorama of the Spongiform Encephalopathies," *Antiviral Chem Chemother* (1990) 1(2):75–84.

You et al., "Amphotericin B Treatment Dissociates in Vivo Replication of the Scrapie Agent from PrP Acumulation" *Nature* (1992)356:598–601.

Agrimi, U. et al., *Medical Hypotheses* 40:113–116 (1993).

*Primary Examiner*—Kevin E. Weddington
*Attorney, Agent, or Firm*—Morrison & Foerster LLP

[57] ABSTRACT

Inhibitors of the Maillard reaction are useful in the treatment or prophylaxis of amyloidosis-based disease, particularly Alzheimer's disease. Particular examples include aminoguanidine and amphotericin B.

8 Claims, No Drawings

USE OF MAILLARD REACTION INHIBITORS FOR THE TREATMENT OF AMYLOIDOSIS-BASED DISEASE

This application is a continuation of U.S. Ser. No. 08/727,597 filed Oct. 11, 1996, and now U.S. Pat. No. 5,891,873 which is the national phase of PCT/GB95/00843 filed Apr. 13, 1995 which claims priority from UK application 94/07305.3 filed Apr. 13, 1994.

This invention relates to preparations of use in the prophylaxis and treatment of amyloidosis-based diseases, including amyloid encephalopathies such as non-senile dementias, in particular Alzheimer's disease.

Alzheimer's disease is a debilitating and eventually fatal disease of mature adults, typically in middle age. The causative agent is not yet understood, but it has similarities to other dementias, in particular scrapie in sheep and Creutzfeldt-Jakob and Gerstmann-Straussler-Scheinker syndromes and bovine spongiform encephlopathy (BSE). These diseases are characterised by the histopathological features of neural amyloidogenesis. Particular examples are the paired helical filaments that form the neurofibrillar tangles in Alzheimer's brains and the fibrils found in scrapie and other spongiform encephalopalopathies. These lesions are derived by modification of normal cellular proteins: tau in the case of Alzheimer's and the prion protein (PrP) in the case of the spongiform encephalopathies. The nature of the modification remains unknown, but leads to amyloid plaques, neuronal degeneration and vacuolation, together with astroglial proliferation.

Similarly, there is no known treatment for these diseases although it has been reported (You et al, Nature, 356, 598–601 (1992)) that the onset of scrapie is delayed in the present of the polyene antibiotic amphotericin B.

We have discovered that amphotericin B unexpectedly acts as an inhibitor for the Maillard reaction. Furthermore we have shown that glycation of soluble tau from Alzheimer's brains leads to the formation of amyloid filaments and that the Maillard reaction inhibitor aminoguanidine inhibits this aggregation. The Maillard reaction comprises the well known degradation of proteins in the-presence of reductive sugars such as glucose to form glycosylated proteins which are implicated in the complications of diabetes such as cataract, nephropathy, retinopathy and atherosclerosis. Various classes of compounds are known to exhibit an inhibiting effect on the Maillard reaction and hence to be of use in the treatment or prophylaxis of the complications of diabetes and in diseases related to old age. Thus, for example, EP-A-0 433 679 describes 4-hydroxy-5,8-dioxoquinoline derivatives of the following formulae (a) a 4-hydroxy-5,8-dioxoquinoline derivative of the formula (I) or a pharmaceutically acceptable salt thereof:

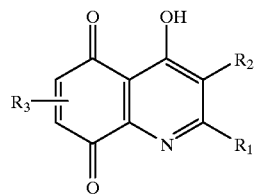

(I)

wherein $R_1$ and $R_2$ are each hydrogen, methyl, trifluoromethyl, carboxy, methoxycarbonyl or ethoxycarbonyl, and $R_3$ is hydrogen or hydroxy;

(b) a 4,5,8-trihydroxyquinoline derivative of the formula (II) or a pharmaceutically acceptable salt thereof:

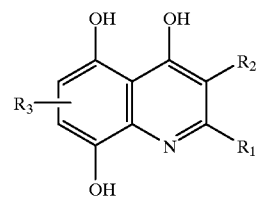

(II)

wherein $R_1$, $R_2$ and $R_3$ are as defined hereinbefore;

(c) a 3-oxophenoxazine derivative of the formula (III) or a pharmaceutically acceptable salt thereof:

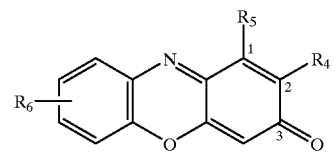

(III)

wherein $R_4$ and $R_5$ are each hydrogen or form by incorporation of $C_1$ and $C_2$ carbon atoms a condensed [2,1-b] pyridine ring optionally substituted with a hydroxyl group and/or a carboxyl group, and R6 is hydrogen or hydroxy; or (d) a 3-oxophenoxazine N-oxide of the formula (IV) or a pharmaceutically acceptable salt thereof:

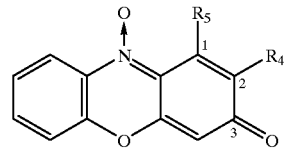

(IV)

wherein $R_4$, $R_5$ and $R_6$ are as defined hereinbefore.

EP-A-0 430 045 similarly discloses ascorbic acid tocopheryl phosphate diesters having Maillard reaction-inhibiting action, namely compounds of the formula:

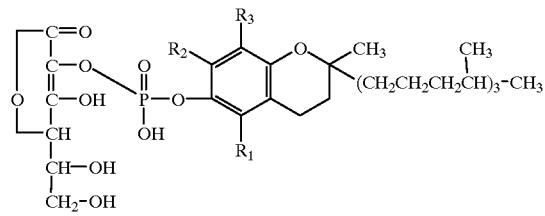

(V)

wherein $R_1$, $R_2$ and $R_3$ independently of one another denote hydrogen or methyl, or a pharmaceutically acceptable salt thereof.

Also EP-A-O 325 936 describes aminoguanidine derivatives of the general formula:

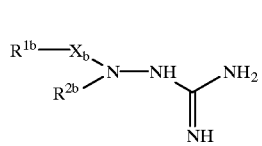

(VI)

(wherein, $R^{1b}$ represents carbocyclic or heterocylic ring substituted or unsubstituted by from 1 to 3 group(s) selected from halogen atom, alkyl or alkoxy group of from 1 to 4 carbon atom(s), nitro group, phenoxy group, amino group, hydroxy group and acylamino group of from 2 to 4 carbon atom(s), $X_b$ represents single-bond, alkylene group of from 1 to 4 carbon atom(s) or alkenylene group of from 2 to 4 carbon atoms, or $R^{1b}$ together with $X_b$ represents alkyl group of from 1 to 4 carbon atom(s), $R^{2b}$ represents hydrogen atom, alkyl group of from 1 to 4 carbon atom(s) or phenyl group substituted or unsubstituted by from 1 to 3 group(s) selected from halogen atom, alkyl or alkoxy group of from 1 to 14 carbon atom(s), hydroxy and nitro group), or an acid addition salt thereof.

According to the present invention we provide the use of a pharmaceutically acceptable Maillard reaction inhibitor in the preparation of a pharmaceutical composition for the treatment or prophylaxis of amyloidosis-based disease, including amyloid encephalopathies such as non-senile dementias, in particular such disease in humans, especially Alzheimer's disease. The invention also provides a method of treatment or prophylaxis of such diseases using the Maillard reaction inhibitors.

The Maillard reaction inhibitors of use may comprise any of the various types mentioned above and also aminoglycosides such as amphotericin B and its analogues, as well as any other pharmaceutically acceptable product which can be shown to inhibit the Maillard reaction in a simple in vitro test.

It is envisaged that the dosage rates of the active materials would be in the same range as those used in the treatment of other conditions, up to a maximum determined by the toxicity of the compound in question.

The following description illustrates the Maillard-inhibitory effect of aminoguanidine and amphotericin B and the evidence for the implication of the Maillard reaction in Alzheimer's paired helical filaments.

EXAMPLE 1

Soluble tau protein isolated from normal or Alzheimer's brains was incubated for 24hr at 37° C. at a concentration of 1 mg/ml in 10 mM reducing sugar solutions in 50 mM phosphate buffer pH 6.8, 1 mM PMSF and 0.1 mM GTP, in the presence or absence of the Maillard reaction inhibitor aminoguanidine. The formation of protein aggregates was analysed by electron microscopy by negative staining. Only soluble tau isolated from Alzheimer's formed aggregates on glycation and this aggregation was inhibited by aminoguanidine. The aggregates formed on glycation by glucose resembled the amyloid fibrils seen in Alzheimer's brains and the Maillard reaction inhibitor, aminoguanidine, inhibited the formation of these filamentous aggregates.

| Sugar | Inhibitor (25 mM) | Normal tau (1 mg/ml) | Alzheimer's tau (1 mg/ml) |
|---|---|---|---|
| None | | No aggregates | No aggregates |
| Glucose | | No aggregates | Filamentous aggregates |
| Glucose | aminoguanidine | No aggregates | No aggregates |
| Fructose | | No aggregates | Few aggregates |
| Fructose | aminoguanidine | No aggregates | No aggregates |

EXAMPLE 2

Bovine serum albumin was dried from solutions containing reducing sugars and incubated at 55° C. for 3 weeks, in the presence or absence of various concentrations of either the Maillard reaction inhibitor aminoguanindine or the antibiotic amphotericin B. The extent of the Maillard reaction was quantified spectrophotometrically by the formation of brown colour. The results showed that the antibiotic amphotericin B, which had previously been shown to delay the onset of scrapie in an animal disease by an unknown mechanism, unexpectedly acted as a Maillard reaction inhibitor similar to aminoguarndine.

| Sugar (25 mM) | Potential Inhibitor | Ratio Sugar: Inhibitor (molar basis) | Absorbance extent of browning |
|---|---|---|---|
| Glucose | None | | 0.709 |
| Glucose | aminoguanidine | 3:1 | 0.603 |
| Glucose | aminoguanidine | 2:1 | 0.205 |
| Glucose | aminoguanidine | 1:1 | 0.212 |
| Glucose | aminoguanidine | 1:2 | 0.211 |
| Glucose | aminoguanidine | 1:3 | 0.154 |
| Non | aminoguanidine | 1:3 | 0.186 |
| Fructose | None | | 2.5 |
| Fructose | aminoguanidine | 1:3 | 0.173 |
| Glucose | None | 1:3 | 0.999 |
| Glucose | amphotericin B | 3:1 | 0.548 |
| Glucose | amphotericin B | 2:1 | 0.349 |
| Glucose | amphotericin B | 1:1 | 0.258 |
| Glucose | amphotericin B | 1:2 | 0.235 |
| Glucose | amphotericin B | 1:3 | 0.206 |
| None | amphotericin B | | 0.205 |
| Fructose | None | | 2.347 |
| Fructose | amphotericin B | 1:3 | 0.224 |

What is claimed is:

1. A method to inhibit the Maillard reaction in a subject afflicted with an amyloidosis-based disease which method comprises administering to said subject a compound of the formula (VI)

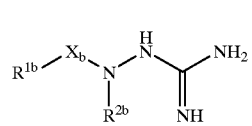

wherein $R^{1b}$ represents carbocyclic or heterocyclic ring substituted or unsubstituted by from 1 to 3 group(s) selected from halogen atom, alkyl or alkoxy group of from 1 to 4 carbon atom(s), nitro group; and the pharmaceutically acceptable salts of compounds of formula VI.

2. The method of claim 1 wherein said compound for formula VI is aminoguanidine.

3. The method of claim 1 wherein the amyloidosis-based disease is a nonsenile dementia.

4. The method of claim 3 wherein said dementia is Alzheimer's Disease.

5. A method to inhibit the Maillard reaction in a subject afflicted with an amyloidosis-based disease which method comprises
administering to said subject a compound of the formula
   a) a compound of the formula

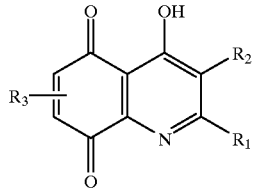

(I)

wherein $R_1$ and $R_2$ are each hydrogen, methyl, trifluoromethyl, carboxy, methoxycarbonyl or ethoxycarbonyl, and $R_3$ is hydrogen or hydroxy; or
   (b) a compound of the formula

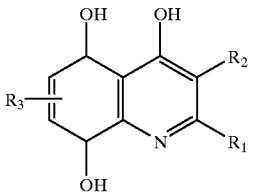

(II)

wherein $R_1$, $R_2$ and $R_3$ are as defined for formula (I); or
   (c) a compound of the formula

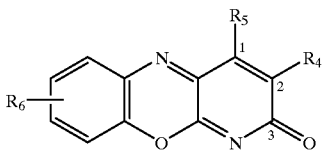

(III)

wherein $R_4$ and $R_5$ are each hydrogen or form by incorporation of $C_1$ and $C_2$ carbon atoms a condensed [2,1-b] pyridine ring optionally substituted with a hydroxyl group and/or a carboxy group, and $R_6$ is hydrogen or hydroxy; or
   (d) a compound of the formula

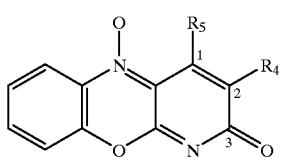

(IV)

wherein $R_4$, $R_5$ and $R_6$ are as defined for formula (III); or
   (e) a compound of the formula

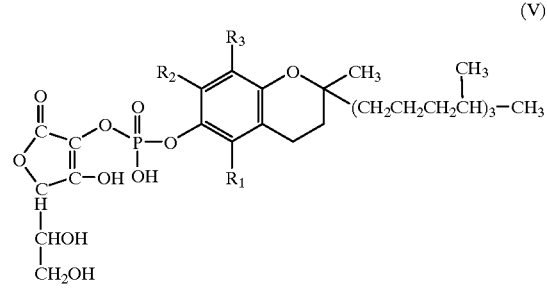

(V)

wherein $R_1$, $R_2$ and $R_3$ independently of one another denote hydrogen or methyl; and the pharmaceutically acceptable salts of compounds of formulas I–V; or amphotericin B.

6. The method of claim 6, in which the Maillard reaction inhibitor comprises amphotericin B.

7. The method of claim 6 wherein the amyloidosis-based disease is a nonsenile dementia.

8. The method of claim 7 wherein said dementia is Alzheimer's Disease.

* * * * *

UNITED STATES PATENT AND TRADEMARK OFFICE
CERTIFICATE OF CORRECTION

PATENT NO.   : 6,034,080
DATED        : March 7, 2000
INVENTOR(S)  : Camilo Colaco et al.

It is certified that error appears in the above-identified patent and that said Letters Patent is hereby corrected as shown below:

Column 4,
Lines 48-65, please delete the claim and substitute therefor:

-- 1. A method to inhibit the Maillard reaction in a subject afflicted with an amyloidosis-based disease which method comprises
administering to said subject a compound of the formula

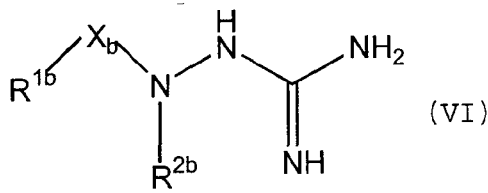

(VI)

wherein $R^{1b}$ represents carbocyclic or heterocyclic ring substituted or unsubstituted by from 1 to 3 group(s) selected from halogen atom, alkyl or alkoxy group of from 1 to 4 carbon atom(s), nitro group, phenoxy group, amino group, hydroxy group and acylamino group of from 2 to 4 carbon atoms(s); $X_b$ represents single-bond, alkylene group of from 1 to 4 carbon atom(s) or alkenylene group of from 2 to 4 carbon atoms, or $R^{1b}$ together with $X_b$ represents alkyl group of from 1 to 4 carbon atom(s); $R^{2b}$ represents hydrogen atom, alkyl group of from 1 to 4 carbon atom(s) or phenyl group unsubstituted or substituted by from 1 to 3 group(s) selected from halogen atom, alkyl or alkoxy group of from 1 to 14 carbon atom(s), hydroxy and nitro group;
and the pharmaceutically acceptable salts of compounds of formula VI. --

Signed and Sealed this

Sixth Day of August, 2002

Attest:

Attesting Officer

JAMES E. ROGAN
*Director of the United States Patent and Trademark Office*